United States Patent
Handa et al.

(10) Patent No.: US 9,724,048 B2
(45) Date of Patent: Aug. 8, 2017

(54) IMAGING CONTROLLER, IMAGING SYSTEM, IMAGING CONTROL METHOD, AND PROGRAM

(71) Applicant: HITACHI, LTD., Tokyo (JP)

(72) Inventors: Takanobu Handa, Tokyo (JP); Kunio Takahashi, Tokyo (JP); Satoshi Muraki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 184 days.

(21) Appl. No.: 14/418,241

(22) PCT Filed: Sep. 12, 2013

(86) PCT No.: PCT/JP2013/074670
§ 371 (c)(1),
(2) Date: Jan. 29, 2015

(87) PCT Pub. No.: WO2014/057762
PCT Pub. Date: Apr. 17, 2014

(65) Prior Publication Data
US 2015/0182175 A1   Jul. 2, 2015

(30) Foreign Application Priority Data

Oct. 9, 2012   (JP) ................................ 2012-224248

(51) Int. Cl.
*A61B 6/00* (2006.01)
*A61B 6/03* (2006.01)
*A61N 5/10* (2006.01)

(52) U.S. Cl.
CPC ............ *A61B 6/032* (2013.01); *A61B 6/4014* (2013.01); *A61B 6/4085* (2013.01); *A61B 6/547* (2013.01);

(Continued)

(58) Field of Classification Search
CPC combination set(s) only.
See application file for complete search history.

(56) References Cited

U.S. PATENT DOCUMENTS

| 2003/0076920 A1* | 4/2003 | Shinno .................... | A61B 6/032 |
| | | | 378/4 |
| 2005/0135550 A1* | 6/2005 | Man ........................ | A61B 6/032 |
| | | | 378/9 |

(Continued)

FOREIGN PATENT DOCUMENTS

| CN | 1846621 A | 10/2006 |
| JP | H04-022343 A | 1/1992 |

(Continued)

OTHER PUBLICATIONS

Europe Patent Office, "Search Report for European Patent Application No. 13845852.6," May 23, 2016.

(Continued)

*Primary Examiner* — Phillip A Johnston
*Assistant Examiner* — Hsien Tsai

(57) ABSTRACT

This imaging controller of the imaging controller includes: an imager position determination section that determines whether or not a first imager is located in an overlapping region where a rotation range of the first imager and a rotation range of a second imager overlap each other when a rotation mechanism rotates the first and second imagers by an angle greater than the predetermined angle; and an imaging timing control section that causes one or both of the first and second imagers to perform imaging when arrival of an imaging timing is detected and that causes only the second imager to perform imaging in at least one imaging timing whose arrival is detected in a state where the imager position determination section determines that the first imager is located in the overlapping region.

5 Claims, 11 Drawing Sheets

(52) U.S. Cl.
CPC ............ *A61N 5/1049* (2013.01); *A61B 6/486* (2013.01); *A61B 6/582* (2013.01); *A61N 5/1081* (2013.01); *A61N 2005/1061* (2013.01)

(56) References Cited

U.S. PATENT DOCUMENTS

| | | | |
|---|---|---|---|
| 2005/0232389 | A1 | 10/2005 | Klingenbeck-Regn |
| 2005/0286679 | A1 | 12/2005 | Sakaguchi et al. |
| 2006/0045235 | A1 | 3/2006 | Bruder et al. |
| 2011/0129060 | A1 | 6/2011 | Handa et al. |
| 2012/0199760 | A1 | 8/2012 | Handa et al. |
| 2012/0207355 | A1 | 8/2012 | Kokubun |

FOREIGN PATENT DOCUMENTS

| | | | |
|---|---|---|---|
| JP | H09-010206 | A | 1/1997 |
| JP | H11-253433 | A | 9/1999 |
| JP | 2001-259059 | A | 9/2001 |
| JP | 2004-121473 | A | 4/2004 |
| JP | 2005-296340 | A | 10/2005 |
| JP | 3743594 | B2 | 2/2006 |
| JP | 2006-122549 | A | 5/2006 |
| JP | 2006-314772 | A | 11/2006 |
| JP | 2007-236760 | A | 9/2007 |
| JP | 4064952 | B2 | 3/2008 |
| JP | 4505639 | B2 | 7/2010 |
| JP | 2011-005159 | A | 1/2011 |
| JP | 2011-050416 | A | 3/2011 |
| JP | 4898901 | B2 | 3/2012 |
| JP | 4959805 | B2 | 6/2012 |
| WO | 2010/073308 | A1 | 7/2010 |
| WO | 2011-030460 | A1 | 3/2011 |
| WO | 2011/055742 | A1 | 5/2011 |
| WO | 2011/059061 | A1 | 5/2011 |

OTHER PUBLICATIONS

China Patent Office, "Office Action for Chinese Patent Application No. 201380039999.4," Jul. 25, 2016.
PCT, "International Search Report for International Application No. PCT/JP2013/074670," Oct. 29, 2013.
PCT, "Written Opinion of the International Searching Authority for International Application No. PCT/JP2013/074670," Oct. 29, 2013.
Japan Patent Office, "Notice of Allowance for JP 2012-224248," Oct. 6, 2015.

\* cited by examiner

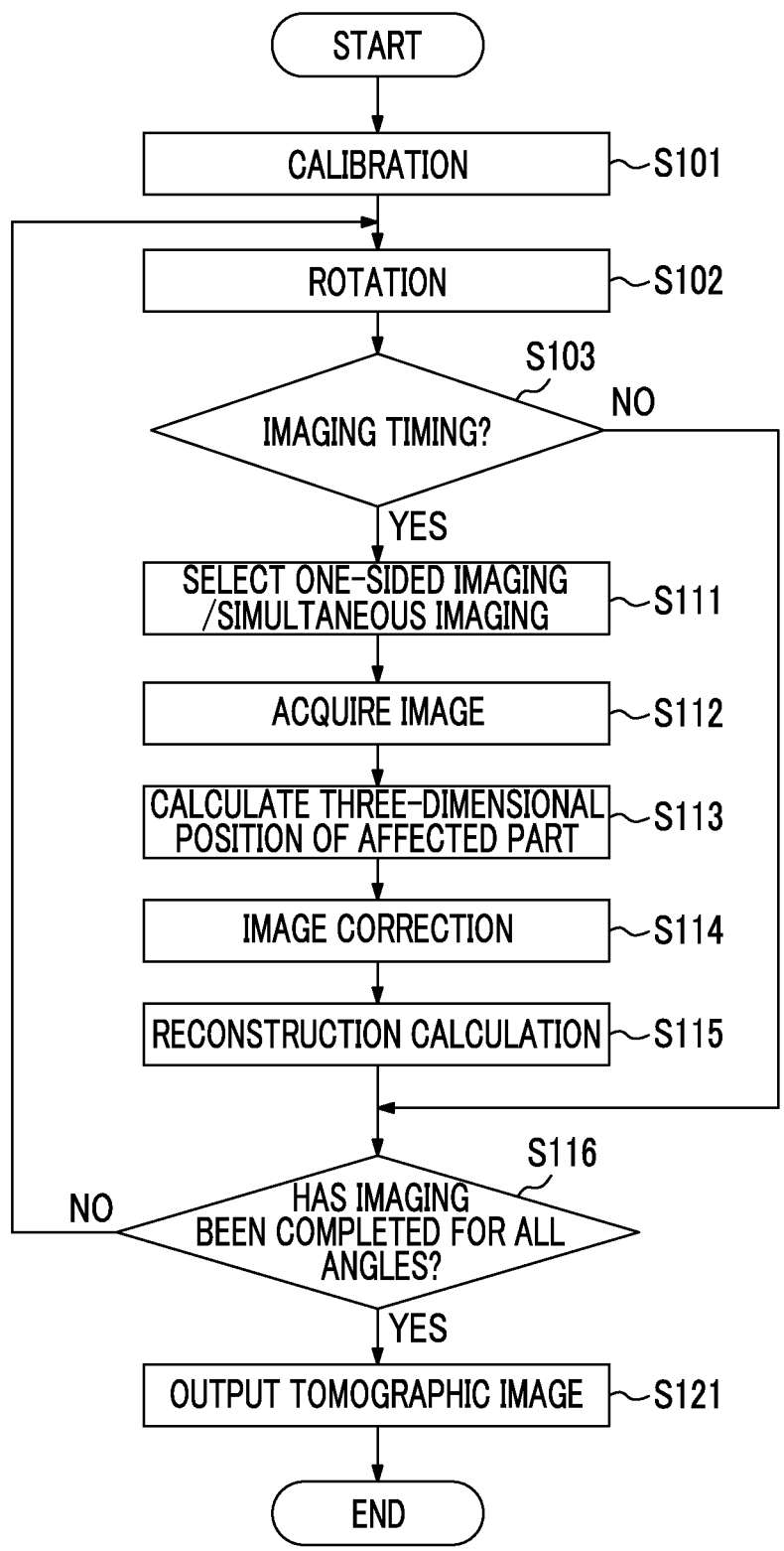

IMAGING CONTROLLER, IMAGING SYSTEM, IMAGING CONTROL METHOD, AND PROGRAM

RELATED APPLICATIONS

The present application is National Phase of International Application No. PCT/JP2013/074670 filed Sep. 12, 2013, and claims priority from Japanese Application No. 2012-224248, filed Oct. 9, 2012, the disclosure of which is hereby incorporated by reference herein in its entirety.

TECHNICAL FIELD

The present invention relates to an imaging controller, an imaging system, an imaging control method, and a program.

Priority is claimed on Japanese Patent Application No. 2012-224248, filed on Oct. 9, 2012, the content of which is incorporated herein by reference.

BACKGROUND ART

In cone beam computed tomography (cone beam CT; CBCT), an imager in which an X-ray source and a two-dimensional detector form a pair captures a two-dimensional radiographic image by emitting cone-shaped X-rays from the X-ray source to the two-dimensional detector while rotating around an imaging target to change the irradiation angle. By using the cone-shaped X-rays, in the cone beam CT, it is possible to generate (reconstruct) a CT image (tomographic image) by capturing a two-dimensional radiographic image without the need to rotate the imaging target during imaging and without the need for multiple rotations.

Here, when performing a CT scan for the human body as a target, if subject blur due to the breathing of the imaging target occurs, this becomes a factor lowering the accuracy of the CT image. In order to prevent such a subject blur, a method is used in which an imaging target holds their breath during imaging. However, an increase in the breath-holding time becomes a burden for the imaging target. Therefore, in order to acquire a high-accuracy image while reducing the burden on the imaging target, it is preferable that the imaging time be short.

As an apparatus capable of reducing the imaging time, there is a CBCT for keeping the relatively small rotation angle of each imager by using a plurality of imagers, such as a dual-source CBCT using two pairs of imagers (for example, PTL 1).

CITATION LIST

Patent Literature

[PTL 1] PCT International Publication No. WO2010/073308

SUMMARY OF INVENTION

Technical Problem

If the radiation dose can be reduced in a CBCT using a plurality of imagers, such as a dual-source CBCT, it is possible to reduce the burden on the imaging target.

The present invention provides an imaging controller, an imaging system, an imaging control method, and a program that can reduce the radiation dose.

Solution to Problem

An imaging controller according to an aspect of the present invention is an imaging controller of an imaging apparatus which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle. The imaging controller includes: an imager position determination section that determines whether or not the first imager is located in an overlapping region where a rotation range of the first imager and a rotation range of the second imager overlap each other when the rotation mechanism rotates the first and second imagers by an angle greater than the predetermined angle; and an imaging timing control section that causes one or both of the first and second imagers to perform imaging when arrival of an imaging timing is detected and that causes only the second imager to perform imaging in at least one imaging timing whose arrival is detected in a state where the imager position determination section determines that the first imager is located in the overlapping region.

In addition, in an imaging controller according to another aspect of the present invention, in the imaging controller described above, a position specifying section that specifies a three-dimensional position of a position specification target based on a radiographic image captured by the first imager and a radiographic image captured by the second imager is included. When the imaging timing control section detects arrival of an imaging timing and causes both of the first and second imagers to perform imaging and the position specifying section succeeds in specifying the three-dimensional position of the position specification target based on the obtained radiographic images, if arrival of a next imaging timing is detected in a state where the imager position determination section determines that the first imager is located in the overlapping region, the imaging timing control section causes only the second imager to perform imaging.

In addition, in an imaging controller according to still another aspect of the present invention, in the imaging controller described above, a position specifying section that specifies a three-dimensional position of a position specification target based on a radiographic image captured by the first imager and a radiographic image captured by the second imager is included. When the imaging timing control section detects arrival of an imaging timing and causes both of the first and second imagers to perform imaging and the position specifying section fails to detect an image of the position specification target in at least one of the obtained radiographic images, if arrival of a next imaging timing is detected in a state where the imager position determination section determines that the first imager is located in the overlapping region, the imaging timing control section causes only the second imager to perform imaging.

In addition, in an imaging controller according to still another aspect of the present invention, in the imaging controller described above, the imaging timing control section causes only the second imager to perform imaging at all imaging timings whose arrival is detected in a state where the imager position determination section determines that the first imager is located in the overlapping region.

In addition, an imaging system according to still another aspect of the present invention includes: an imaging apparatus which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle; and an imaging controller configured to include an imager position determination section that determines whether or not the first imager is located in an overlapping region where a rotation range of the first imager and a rotation range of the second imager overlap each other when the rotation mechanism rotates the first and second imagers by an angle greater than the predetermined angle and an imaging timing control section that causes one or both of the first and second imagers to perform imaging when arrival of an imaging timing is detected and that causes only the second imager to perform imaging in at least one imaging timing whose arrival is detected in a state where the imager position determination section determines that the first imager is located in the overlapping region.

In addition, an imaging control method according to still another aspect of the present invention is an imaging control method of an imaging controller of an imaging apparatus which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle. The imaging control method includes: an imager position determination step of determining whether or not the first imager is located in an overlapping region where a rotation range of the first imager and a rotation range of the second imager overlap each other when the rotation mechanism rotates the first and second imagers by an angle greater than the predetermined angle; and an imaging timing control step of causing one or both of the first and second imagers to perform imaging when arrival of an imaging timing is detected and causing only the second imager to perform imaging in at least one imaging timing whose arrival is detected in a state where it is determined that the first imager is located in the overlapping region in the imager position determination step.

In addition, a program according to still another aspect of the present invention is a program causing a computer as an imaging controller of an imaging apparatus, which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle, to execute: an imager position determination step of determining whether or not the first imager is located in an overlapping region where a rotation range of the first imager and a rotation range of the second imager overlap each other when the rotation mechanism rotates the first and second imagers by an angle greater than the predetermined angle; and an imaging timing control step of causing one or both of the first and second imagers to perform imaging when arrival of an imaging timing is detected and causing only the second imager to perform imaging in at least one imaging timing whose arrival is detected in a state where it is determined that the first imager is located in the overlapping region in the imager position determination step.

Advantageous Effects of Invention

According to the imaging controller, the imaging system, the imaging control method, and the program described above, it is possible to reduce the radiation dose.

BRIEF DESCRIPTION OF DRAWINGS

FIG. 12 is a flowchart showing the procedure of the process performed by an imaging processing unit in the present embodiment.

DESCRIPTION OF EMBODIMENTS

Hereinafter, the present invention will be described through embodiments of the invention. However, the following embodiments are not intended to limit the invention defined in the appended claims. In addition, all combinations of the features described in the embodiments are not necessary for the solving means of the invention.

Figure 1:
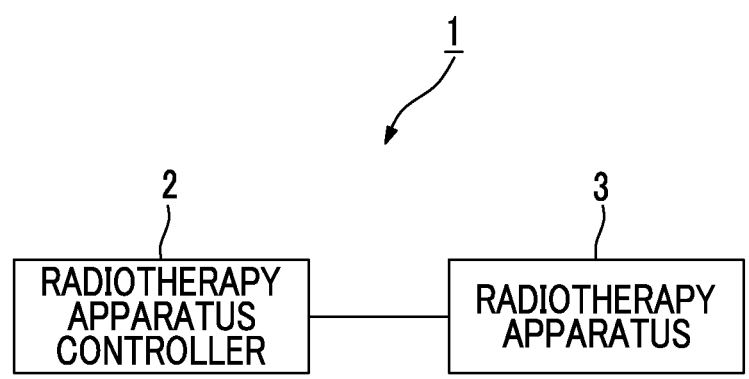
FIG. 1 is a schematic block diagram showing the functional configuration of an imaging system in an embodiment of the present invention.

FIG. 1 is a schematic block diagram showing the functional configuration of an imaging system in an embodiment of the present invention. In this diagram, a radiotherapy system 1 includes a radiotherapy apparatus controller 2 and a radiotherapy apparatus 3.

The radiotherapy system 1 performs the emission (emission of radiation toward a certain target, such as an affected part) of radiation (may be a heavy particle beam) in radiation therapy or the generation of a CT image (tomographic image) for treatment planning. The radiotherapy system 1 corresponds to an example of an imaging system in the present embodiment.

The radiotherapy apparatus 3 emits radiation to the affected part in radiation therapy. In addition, the radiotherapy apparatus 3 captures a radiographic image (X-ray radiographic image) in order to generate a CT image. The radiotherapy apparatus 3 corresponds to an example of an imaging apparatus in the present embodiment.

The radiotherapy apparatus controller 2 controls the radiotherapy apparatus 3 to emit radiation and capture a radiographic image. In addition, the radiotherapy apparatus controller 2 generates a CT image based on the radiographic image captured by the radiotherapy apparatus 3. The radiotherapy apparatus controller 2 corresponds to an example of an imaging controller in the present embodiment.

Figure 2:
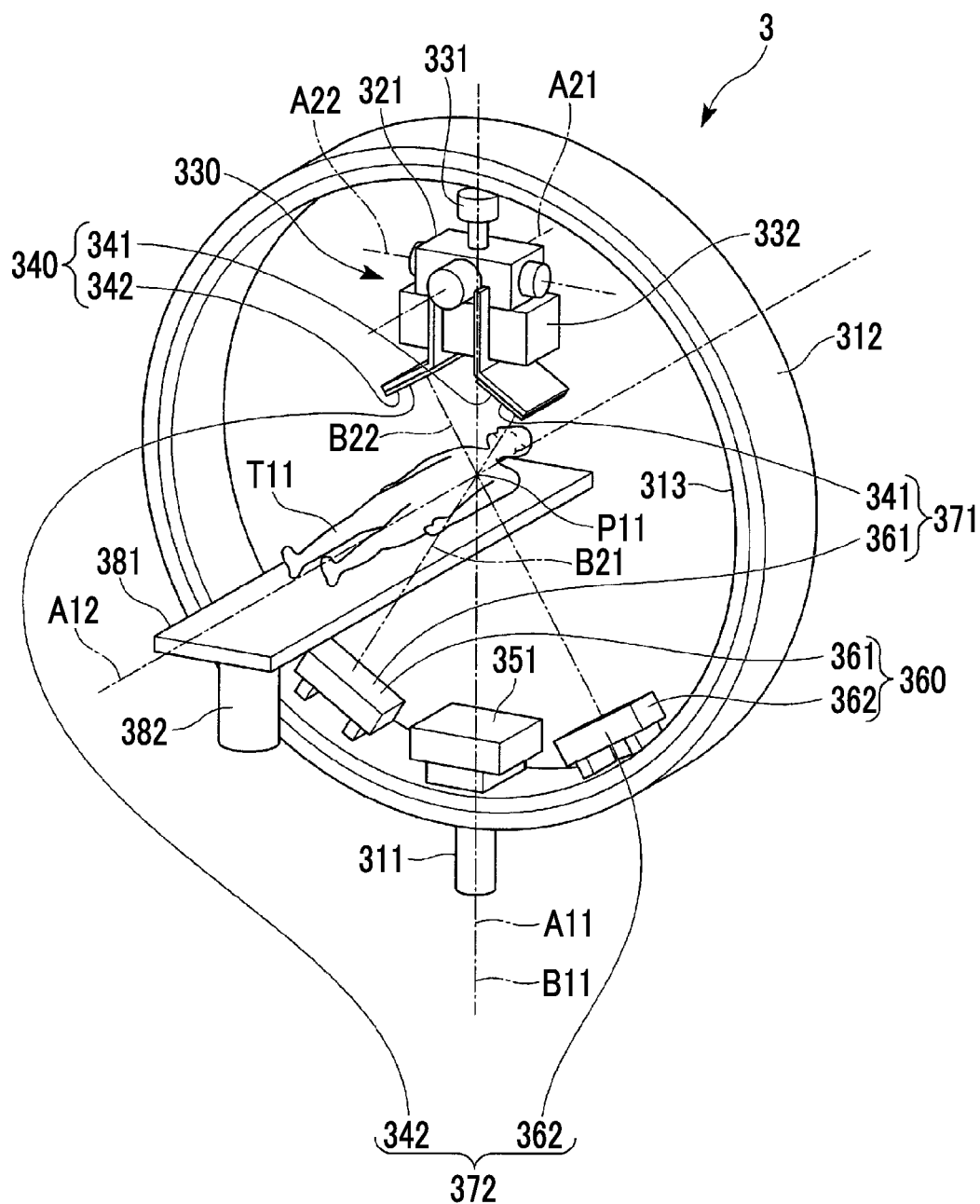
FIG. 2 is a schematic diagram showing the apparatus configuration of a radiotherapy apparatus in the present embodiment.

FIG. 2 is a schematic diagram showing the apparatus configuration of the radiotherapy apparatus 3. In this diagram, the radiotherapy apparatus 3 includes a rotary driving unit 311, an O ring 312, a traveling gantry 313, a swing mechanism 321, an irradiation unit 330, a sensor array 351, a sensor array 361, a sensor array 362, a couch 381, and a couch driving unit 382. The irradiation unit 330 includes a therapeutic radiation emission unit 331, a multi-leaf collimator (MLC) 332, a diagnostic X-ray source 341, and a diagnostic X-ray source 342.

The diagnostic X-ray source 341 and diagnostic X-ray source 342 will be referred to collectively as a "diagnostic X-ray source 340" hereinafter. In addition, the sensor array 361 and the sensor array 362 will be referred to collectively as a "sensor array 360" hereinafter.

The rotary driving unit 311 supports the O ring 312 on a base so as to be able to rotate around a rotation axis A11, and rotates the O ring 312 according to the control of the radiotherapy apparatus controller 2. The rotation axis A11 is an axis in a vertical direction.

The O ring 312 is formed in a ring shape having a rotation axis A12 at the center, and supports the traveling gantry 313 so as to be able to rotate around the rotation axis A12. The rotation axis A12 is an axis in a horizontal axis (that is, an axis perpendicular to the vertical direction), and is perpendicular to the rotation axis A11 at the isocenter P11. The rotation axis A12 is fixed to the O ring 312. That is, the rotation axis A12 rotates around the rotation axis A11 with the rotation of the O ring 312.

The traveling gantry 313 is formed in a ring shape having the rotation axis A12 at the center, and is disposed inside the O ring 312 so as to be concentric with the O ring 312. The radiotherapy apparatus 3 further includes a traveling driving device (not shown), and the traveling gantry 313 rotates around the rotation axis A12 with power from the traveling driving device.

The traveling gantry 313 itself is rotated to integrally rotate each unit provided in the traveling gantry 313, such as the diagnostic X-ray source 341 and the sensor array 361 or the diagnostic X-ray source 342 and the sensor array 362.

The traveling gantry 313 corresponds to an example of a rotation mechanism in the present embodiment.

The swing mechanism 321 is fixed inside the ring of the traveling gantry 313, and supports the irradiation unit 330 on the traveling gantry 313. The swing mechanism 321 rotates the irradiation unit 330 around a pan axis A21 and rotates the irradiation unit 330 around a tilt axis A22 according to the control of the radiotherapy apparatus controller 2.

The pan axis A21 is an axis parallel to the rotation axis A12, and is fixed to the traveling gantry 313. The swing mechanism 321 causes the irradiation unit 330 to perform a swinging operation to the left and right with respect to the rotation axis A12 (accordingly, to the left and right with respect to an imaging target T11 shown in FIG. 2) by rotating the irradiation unit 330 around the pan axis A21.

The tilt axis A22 is an axis perpendicular to the pan axis A21, and is fixed to the traveling gantry 313. The swing mechanism 321 causes the irradiation unit 330 to perform a swinging operation in a direction of the rotation axis A12 (accordingly, up and down with respect to the imaging target T11) by rotating the irradiation unit 330 around the tilt axis A22.

The irradiation unit 330 is disposed inside the traveling gantry 313 so as to be supported by the swing mechanism 321, and emits therapeutic radiation B11 or a diagnostic X-ray B21 or B22.

The therapeutic radiation emission unit 331 emits the therapeutic radiation B11 according to the control of the radiotherapy apparatus controller 2. The therapeutic radiation emission unit 331 is supported by the traveling gantry 313 through the swing mechanism 321. For this reason, once the therapeutic radiation emission unit 331 is directed toward the isocenter P11 by adjustment of the swing mechanism 321, the therapeutic radiation B11 always passes through the isocenter P11 in general even if the O ring 312 is rotated by the rotary driving unit 311 and even if the traveling gantry 313 is rotated by the traveling driving device. Therefore, the therapeutic radiation emission unit 331 can emit the therapeutic radiation B11 toward the isocenter P11 from various directions by rotating around the rotation axis A11 or the rotation axis A12.

In addition, a case where deflection occurs in the traveling gantry 313 due to the weight of the irradiation unit 330 or the like or a case where the affected part to be irradiated does not necessarily match the isocenter P11 may occur. In this case, after the therapeutic radiation emission unit 331 rotates around the rotation axis A11 or the rotation axis A12, the swing mechanism 321 corrects the direction of the therapeutic radiation emission unit 331. Accordingly, it is possible to perform high-accuracy positioning.

The multi-leaf collimator 332 matches the shape of the radiation field when the therapeutic radiation B11 is emitted to the patient with the shape of the affected part by shielding a part of the therapeutic radiation B11 according to the control of the radiotherapy apparatus controller 2.

The diagnostic X-ray source 341 emits the diagnostic X-ray B21 toward the isocenter P11 according to the control of the radiotherapy apparatus controller 2. The diagnostic X-ray B21 is a cone beam that is emitted from one point of the diagnostic X-ray source 341 and that has a conical shape, such as a cone or a pyramid, with the one point as an apex.

The diagnostic X-ray source 342 emits the diagnostic X-ray B22 toward the isocenter P11 according to the control of the radiotherapy apparatus controller 2. The diagnostic X-ray B22 is a cone beam that is emitted from one point of the diagnostic X-ray source 342 and that has a conical shape, such as a cone or a pyramid, with the one point as an apex.

Figure 3:
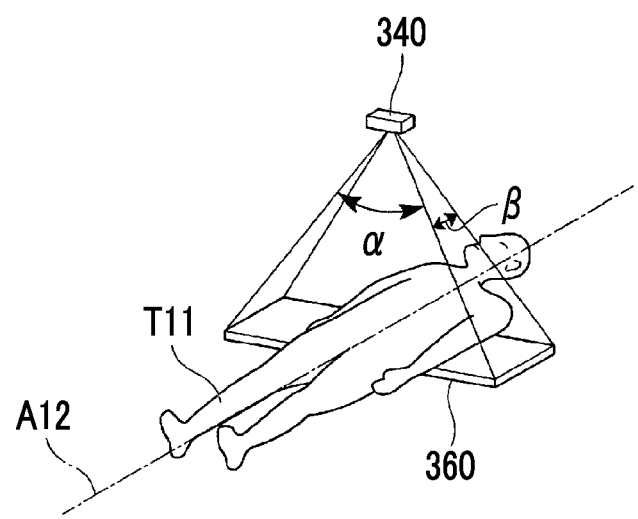
FIG. 3 is an explanatory diagram showing an example of the cone beam emitted from a diagnostic X-ray source in the present embodiment.

FIG. 3 is an explanatory diagram showing an example of the cone beam emitted from the diagnostic X-ray source 340. As shown in the diagram, the cone beam emitted from the diagnostic X-ray source 340 spreads in both of the direction perpendicular to the rotation axis A12 (left and right direction of the imaging target T11) and the direction of the rotation axis A12 (up and down direction of the imaging target T11). Hereinafter, a fan angle, which is an angle indicating the spread of a cone beam in a direction perpendicular to the rotation axis A12, is expressed as "α". In addition, a cone angle, which is an angle indicating the spread of a cone beam in a direction of the rotation axis A12 is expressed as "β".

In FIG. 2, both of the diagnostic X-rays B21 and B22 are shown as the irradiation axis. The irradiation axis of the cone beam referred to herein is the central axis of the cone formed by the cone beam (for example, when the cone beam has a conical shape, the rotation axis of the cone).

The diagnostic X-ray sources 341 and 342 are fixed to the irradiation unit 330 (for example, a housing of the multi-leaf collimator 332) in a direction perpendicular to the irradiation axis. In particular, when the therapeutic radiation emission unit 331 is directed toward the isocenter P11 (that is, when the therapeutic radiation emission unit 331 is directed toward a direction in which the therapeutic radiation B11 passes through the isocenter P11), the irradiation axis of the diagnostic X-ray source 341 and the irradiation axis of the diagnostic X-ray source 342 are perpendicular to each other at the isocenter P11.

The sensor array 351 is disposed at a position hit by the therapeutic radiation B11 from the therapeutic radiation emission unit 331 so as to face the therapeutic radiation emission unit 331, and is fixed inside the ring of the traveling gantry 313. The sensor array 351 receives the therapeutic radiation B11, which is emitted from the therapeutic radiation emission unit 331 and is transmitted through the subject, such as the affected part, and generates (captures) a radiographic image (radiation projection image) of the subject. The radiographic image of the subject generated by the sensor array 351 is used when checking the radiation position of the therapeutic radiation B11, when recording the treatment, and the like. Reception referred to herein is receiving the radiation.

As the sensor array 351, it is possible to use various devices that can receive the therapeutic radiation B11 and generate a radiographic image. For example, the sensor array 351 may be a flat panel detector (FPD), or may be an X-ray image intensifier (II).

The sensor array 361 is disposed at a position hit by the diagnostic X-ray B21 from the diagnostic X-ray source 341 so as to face the diagnostic X-ray source 341, and is fixed inside the ring of the traveling gantry 313. The sensor array 361 receives the diagnostic X-ray B21, which is emitted from the diagnostic X-ray source 341 and is transmitted through the subject, such as the affected part, and generates a radiographic image of the subject. The radiographic image of the subject generated by the sensor array 361 and the radiographic image of the subject generated by the sensor array 362 are used when the radiotherapy apparatus controller 2 generates a CT image.

As the sensor array 361, it is possible to use various devices that can receive the diagnostic X-ray B21 and generate a radiographic image. For example, the sensor array 361 may be an FPD, or may be an X-ray II.

The sensor array 362 is disposed at a position hit by the diagnostic X-ray B22 from the diagnostic X-ray source 342 so as to face the diagnostic X-ray source 342, and is fixed inside the ring of the traveling gantry 313. The sensor array 362 receives the diagnostic X-ray B22, which is emitted from the diagnostic X-ray source 342 and is transmitted through the subject, such as the affected part, and generates a radiographic image of the subject. The radiographic image of the subject generated by the sensor array 362 and the radiographic image of the subject generated by the sensor array 361 are used when the radiotherapy apparatus controller 2 generates a CT image.

As the sensor array 362, it is possible to use various devices that can receive the diagnostic X-ray B22 and generate a radiographic image. For example, the sensor array 362 may be an FPD, or may be an X-ray II.

When the traveling gantry 313 is made to travel along the O ring 312, the diagnostic X-ray source 341 and the sensor array 361, the diagnostic X-ray source 342 and the sensor array 362, and the therapeutic radiation emission unit 331 and the sensor array 351 rotate around the rotation axis A12 passing through the isocenter P11 while maintaining the positional relationship therebetween.

Hereinafter, the combination of the diagnostic X-ray source 341 and the sensor array 361 is referred to as an "imager 371", and the combination of the diagnostic X-ray source 342 and the sensor array 362 is referred to as an "imager 372". Each of the imager 371 and the imager 372 corresponds to an example of an imager in the present embodiment. That is, the diagnostic X-ray source 341 emits the diagnostic X-ray B21 of a cone beam toward the rotation axis A12, and the sensor array 361 captures a radiographic image based on the diagnostic X-ray B21. In addition, the diagnostic X-ray source 342 emits the diagnostic X-ray B22 of a cone beam toward the rotation axis A12, and the sensor array 362 captures a radiographic image based on the diagnostic X-ray B22.

Here, emitting the cone beam toward the rotation axis is emitting the cone beam so that the cone beam and the rotation axis cross each other. Typically, the cone beam is emitted so that the irradiation axis of the cone beam and the rotation axis cross each other. However, the embodiment of the present invention is not limited to this.

Hereinafter, a case where the imager 371 is an example of a first imager and the imager 372 is an example of a second imager will be described as an example. However, the embodiment of the present invention is not limited to this. The imager 372 may be an example of the first imager, and the imager 371 may be an example of the second imager.

In addition, an angle between the irradiation axis of the imager 371 and the irradiation axis of the imager 372 is fixed at a predetermined angle with the rotation axis A12 as a reference. In addition, the irradiation axis of the imager referred to herein is the irradiation axis of the cone beam emitted from the imager.

More specifically, when the swing mechanism 321 sets the direction of the irradiation unit 330 so that the therapeutic radiation B11 passes through the isocenter P11, the irradiation axis of the diagnostic X-ray B21 and the irradiation axis of the diagnostic X-ray B22 are perpendicular to each other at the isocenter P11 of the rotation axis A12. Also when the traveling gantry 313 rotates, the imager 371 (the diagnostic X-ray source 341 and the sensor array 361) and the imager 372 (the diagnostic X-ray source 342 and the sensor array 362) rotate while keeping the irradiation axes perpendicular to each other. In this regard, the traveling gantry 313 rotates the imager 371 and the imager 372 integrally.

In addition, as will be described later, the angle between the diagnostic X-ray B21 and the diagnostic X-ray B22 is not limited to 90°.

The couch 381 is used for the lying down of the imaging target T11 who is a patient to be treated. The couch 381 includes a fixture (not shown). By fixing the imaging target T11 to the couch 381 using a fixed portion, it is possible to reduce subject blur (image blur due to subject movement) when the diagnostic X-ray source 340 emits a diagnostic X-ray to capture a radiographic image or the shift of the radiation position when the therapeutic radiation emission unit 331 emits the therapeutic radiation B11.

The couch driving unit 382 supports the couch 381 on a base, and moves the couch 381 according to the control of the radiotherapy apparatus controller 2. By moving the couch 381 using the couch driving unit 382, it is possible to locate the affected part of the imaging target T11 at the isocenter P11 or near the isocenter P11.

Figure 4:
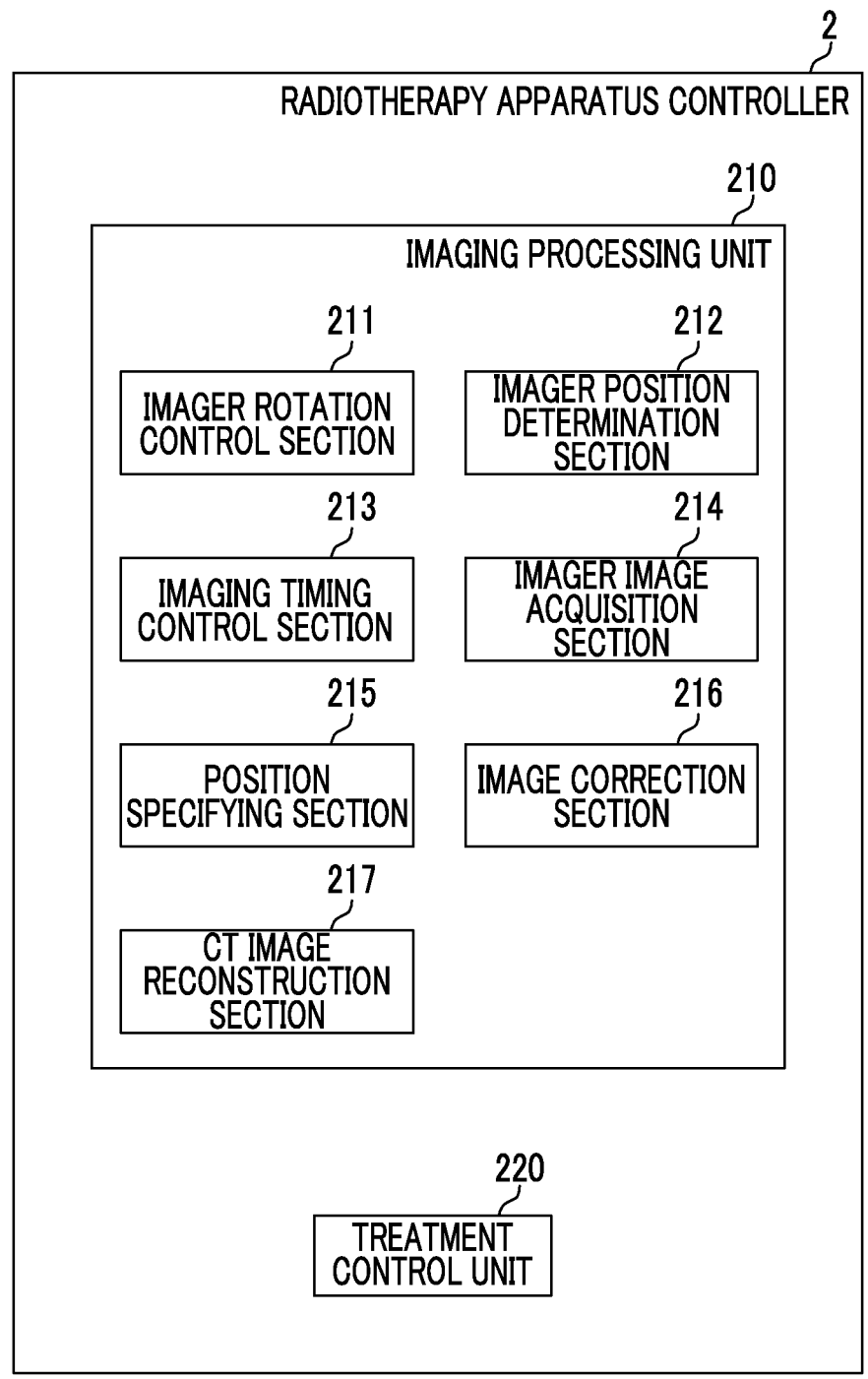
FIG. 4 is a schematic block diagram showing the functional configuration of a radiotherapy apparatus control device in the present embodiment.

FIG. 4 is a schematic block diagram showing the functional configuration of the radiotherapy apparatus controller 2. In this diagram, the radiotherapy apparatus controller 2 includes an imaging processing unit 210 and a treatment control unit 220. The imaging processing unit 210 includes an imager rotation control section 211, an imager position determination section 212, an imaging timing control section 213, an imager image acquisition section 214, a position specifying section 215, an image correction section 216, and a CT image reconstruction section 217.

The imaging processing unit 210 controls the radiotherapy apparatus 3 (FIG. 2) to acquire a radiographic image of the imaging target T11, and generates a CT image based on the acquired radiographic image.

The CT image reconstruction section 217 generates (reconstructs) a CT image from the radiographic image that has been captured by the sensor array 360 and has an affected part position corrected by the image correction section 216 as will be described later. In addition, as the affected part position, for example, the center-of-gravity position corresponding to the shape (area) of the affected part image can be used.

Figure 5A:
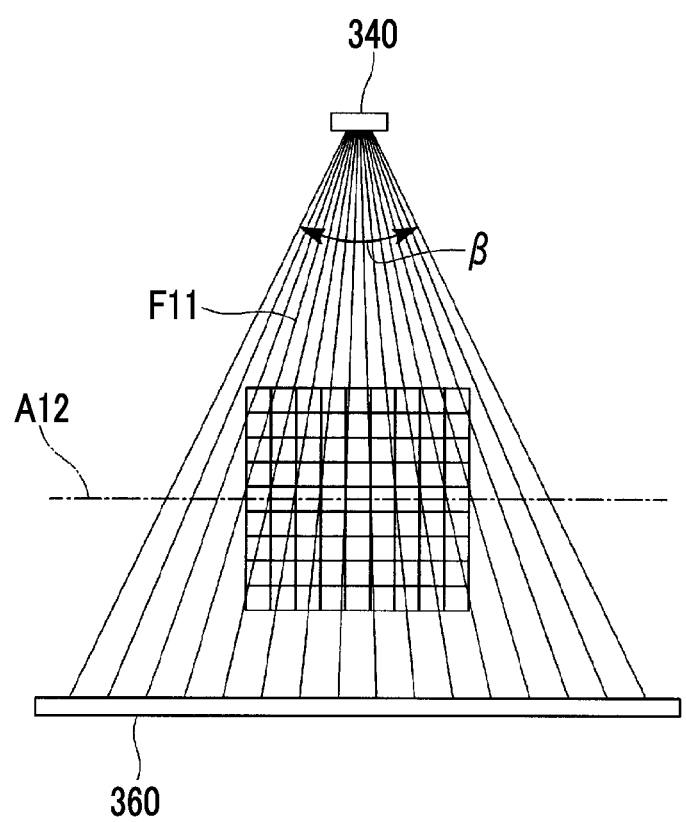
FIG. 5A is an explanatory diagram of the reconstruction of a CT image that is performed by a CT image reconstruction section in the present embodiment.
Figure 5B:
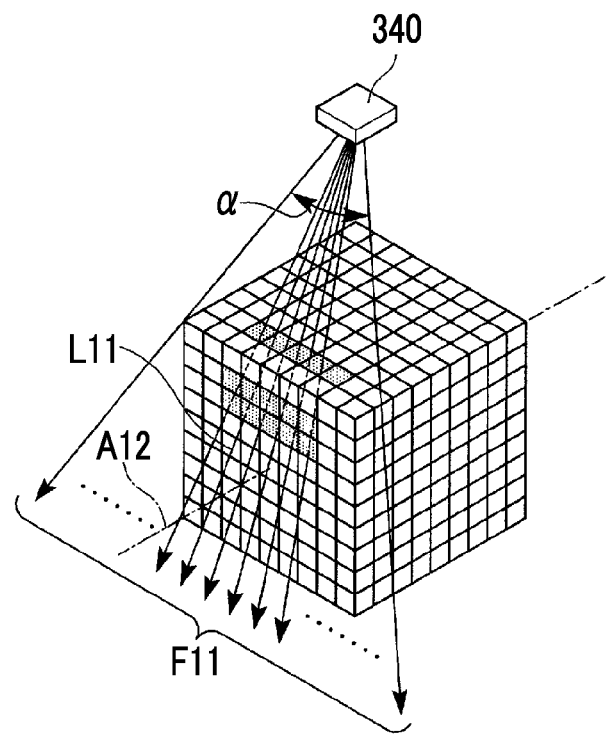
FIG. 5B is an explanatory diagram of the reconstruction of a CT image that is performed by the CT image reconstruction section in the present embodiment.
Figure 5C:
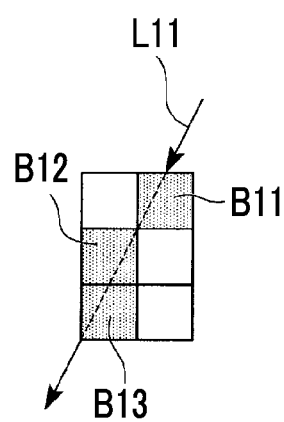
FIG. 5C is an explanatory diagram of the reconstruction of a CT image that is performed by the CT image reconstruction section in the present embodiment.

FIGS. 5A to 5C are explanatory diagrams of the reconstruction of a CT image that the CT image reconstruction section 217 performs. As described with reference to FIG. 3, the cone beam emitted from the diagnostic X-ray source 340 has a spread of the fan angle α and the cone angle β. Therefore, the cone beam emitted from the diagnostic X-ray source 340 is projected onto the light receiving surface (surface that receives X-rays) of the sensor array 360 in a two-dimensional manner (for example, in a rectangular area of the light receiving surface of the sensor array 360).

Here, the light receiving surface of the sensor array 360 is divided into pixels, and the CT image reconstruction section 217 acquires the density information of each pixel as radiographic image data. The density information indicates the intensity of the X-ray received by each pixel of the sensor array 360 (value after the correction of the image correction section 216). Hereinafter, the pixel of the light receiving surface of the sensor array 360 is referred to as a "pixel of the sensor array 360".

In addition, the space of a target whose CT image is to be generated is classified into voxels corresponding to the pixels of the sensor array 360. The CT image reconstruction section 217 converts the X-ray intensity of each pixel into the total value of the X-ray transmittance in each voxel through which the X-rays pass. Hereinafter, the process of converting the X-ray intensity of each pixel into the total value of the X-ray transmittance in each voxel through which the X-rays pass is referred to as "back projection".

FIG. 5A shows X-rays, which are emitted to the row of pixels of the sensor array 360, as a surface, such as a surface F11. The row of pixels referred to herein is the arrangement of pixels in a direction perpendicular to the rotation axis A12 (in the left and right direction of the imaging target T11 shown in FIG. 2). In addition, since FIG. 5A shows a state when viewed from the direction perpendicular to the rotation axis A12, each surface is shown by a line.

FIG. 5B shows X-rays, which are emitted to the respective pixels of the sensor array 360, as lines, such as line L11, in relation to the surface F11.

In addition, FIG. 5C shows voxels through which line L11 passes. Line L11 passes through voxels B11, B12, and B13, and the CT image reconstruction section 217 performs back projection of the X-ray intensity in a pixel corresponding to line L11 onto the total value of the X-ray transmittances of the voxels B11, B12, and B13.

The CT image reconstruction section 217 acquires a radiographic image by projecting X-rays onto the subject (affected part of the imaging target T11) from various angles, and performs back projection for each pixel of the sensor array 360 for each radiographic image.

Then, the CT image reconstruction section 217 calculates the X-ray transmittance of each voxel based on the obtained total value of the X-ray transmittances from various angles, and generates a CT image based on the obtained X-ray transmittance of each voxel.

In addition, each quantity or the positional relationship shown in FIGS. 5A to 5C is an example for explanation, and the present invention is not limited thereto. For example, the fan angle α and the cone angle β of the cone beam emitted from the diagnostic X-ray source 340, the number of pixels of the sensor array 360, the number of voxels set in the space of the target whose CT image is to be generated, or the positional relationship between the diagnostic X-ray source 340 or the sensor array 360 and the voxels is not limited to those shown in FIGS. 5A to 5C.

The imager rotation control section 211 controls the traveling driving device of the radiotherapy apparatus 3 to rotate the traveling gantry 313, thereby rotating the diagnostic X-ray source 341 and the sensor array 361 or the diagnostic X-ray source 342 and the sensor array 362. Here, in order for the CT image reconstruction section 217 to generate a high-accuracy CT image by performing back projection, radiographic images of the subject from many angles are required. Therefore, the imager rotation control section 211 rotates the imager 371 and the imager 372 to locate the subject at various angles.

Figure 6:
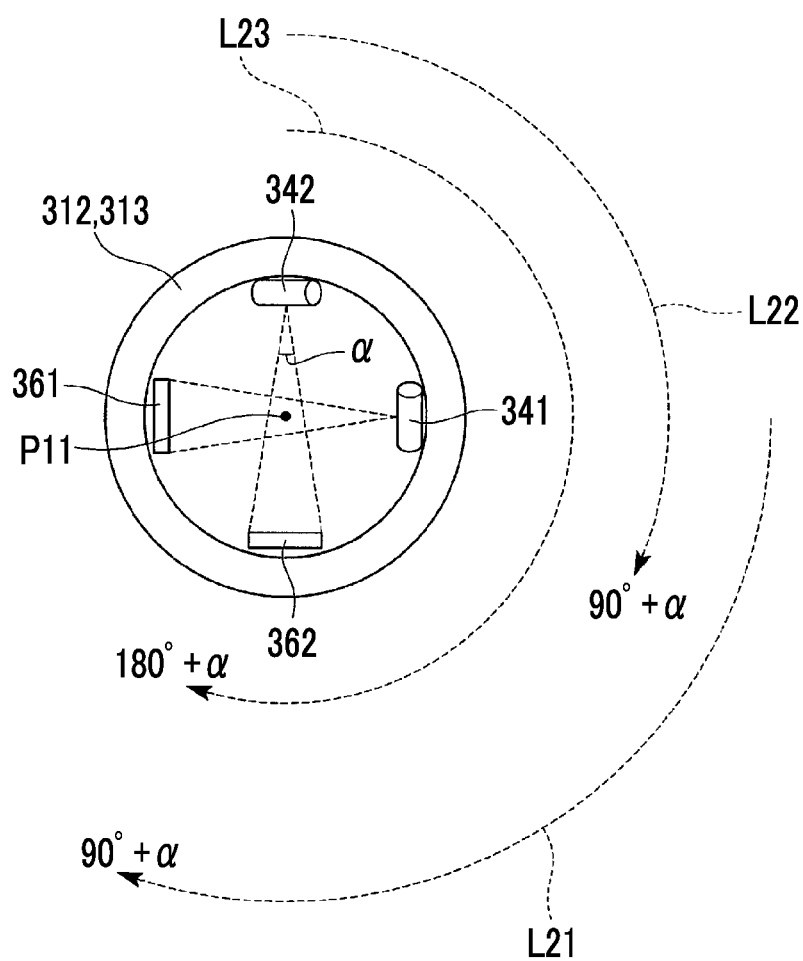
FIG. 6 is an explanatory diagram showing an example of the angle by which an imager is rotated by an imager rotation control section in the present embodiment.

FIG. 6 is an explanatory diagram showing an example of the angle by which the imager rotation control section 211 rotates an imager. Line L21 shown in this diagram indicates the rotation range of the imager 371, and line L22 indicates the rotation range of the imager 372. In addition, line L23 indicates a combined range of the rotation range of the imager 371 and the rotation range of the imager 372.

As described with reference to FIG. 2, the diagnostic X-ray source 341 and the diagnostic X-ray source 342 are disposed such that the irradiation axes thereof are perpendicular to each other. For this reason, when the imager rotation control section 211 controls the traveling driving device of the radiotherapy apparatus 3 to rotate the traveling gantry 313 by 90° or more, the rotation range of the imager 371 and the rotation range of the imager 372 overlap each other. Therefore, if the rotation range of the imager 371 and the rotation range of the imager 372 are combined, it is possible to rotate the subject in the range of an angle of 180° or more with respect to the subject. Thus, since the imager can be rotated in the range of an angle of 180° or more with respect to the subject by rotating the traveling gantry 313 by 90° or more, the imaging time can be reduced to approximately half of that when there is one imager.

Here, as shown in FIG. 6, the imager rotation control section 211 rotates the traveling gantry 313 (accordingly, the imager 371 and the imager 372) by 90°+fan angle α (by an angle obtained by adding the fan angle α to 90°). Therefore, the traveling gantry 313 rotates the imager 371 and the imager 372 by an angle greater than 90° (angle between the irradiation axis of the imager 371 and the irradiation axis of the imager 372 when the rotation axis A12 is a reference). This will be described with reference to FIG. 7.

Figure 7:
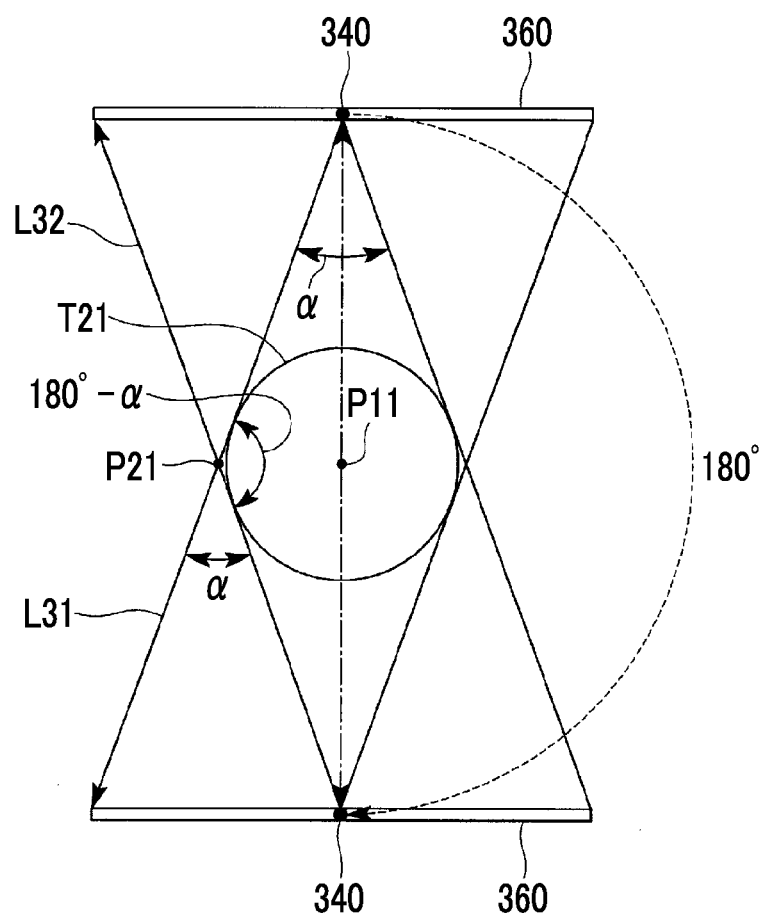
FIG. 7 is an explanatory diagram showing the angle of an X-ray passing through the end of the fan angle of a cone beam when the rotation range of the imager is 180° in the present embodiment.

FIG. 7 is an explanatory diagram showing the angle of an X-ray passing through the end of the fan angle of a cone beam when the rotation range of the imager is 180°. A point P21 shown in this diagram is located on line L31 at the end of the fan angle α of the cone beam, which is emitted from the diagnostic X-ray source 340, when the diagnostic X-ray source 340 starts to rotate. When the diagnostic X-ray source 340 is present at a position rotated by 180° from the position at the start of rotation, the point P21 is located on line L32 at the end of the fan angle α of the cone beam emitted from the diagnostic X-ray source 340.

As shown in FIG. 7, the direction of the X-ray passing through the point P21 changes in a range of an angle obtained by subtracting the fan angle α from 180°. On the other hand, in order for the CT image reconstruction section 217 to generate a high-accuracy CT image, it is preferable to acquire information (density information of each pixel of the sensor array 360) by emitting X-rays to all voxels from the respective directions in the range of 180° or more.

Therefore, the imager rotation control section 211 controls the traveling driving device to rotate the traveling gantry 313 by 90°+fan angle α. Then, the combined rotation range of the rotation range of the imager 371 and the rotation range of the imager 372 becomes 180°+fan angle α. Accordingly, the CT image reconstruction section 217 can acquire the information by emitting X-rays to all voxels from the respective directions in the range of 180° or more.

The imager position determination section 212 acquires the position information of the imager 371 (information indicating the amount of rotation of the imager 371), and determines whether or not the imager 371 is located in an overlapping region where the rotation range of the imager 371 and the rotation range of the imager 372 overlap each other (hereinafter, simply referred to as an "overlapping region").

Here, as a method used when the imager position determination section 212 acquires the position information of the imager 371, it is possible to use various methods. For example, the imager position determination section 212 may acquire the control information of the traveling driving device from the imager rotation control section 211, and calculate the rotation angle from the reference position (for example, the position at the start of rotation) of the diagnostic X-ray source 340, as the position information of the imager 371, based on the control information. Alternatively, when a shift occurs between the control information from the imager rotation control section 211 and the actual rotation angle of the traveling gantry 313, the traveling gantry 313 may measure the rotation angle, and the imager position determination section 212 may acquire the rotation angle as the position information of the imager 371 (rotation angle of the imager 371).

In addition, the imager position determination section 212 determines whether or not the imager 371 is located in the overlapping region by determining whether or not the amount of rotation of the imager 371 is equal to or greater than 90° based on the position information of the imager 371. That is, when the amount of rotation of the imager 371 is equal to or greater than 90°, the imager 371 is located in the overlapping region.

The imaging timing control section 213 causes one or both of the imager 371 and the imager 372 to perform imaging when detecting the arrival of imaging timing. Specifically, the imaging timing control section 213 outputs control information instructing one or both of the imager 371 and the imager 372 to perform imaging every time set in advance as an imaging period.

In this case, the imaging timing control section 213 causes only the imager 372 to perform imaging in at least one imaging timing whose arrival is detected in a state where the imager position determination section 212 determines that the imager 371 is located in the overlapping region. For example, the imaging timing control section 213 causes only the imager 372 to perform imaging at all of the imaging timings whose arrival is detected in a state where the imager position determination section 212 determines that the imager 371 is located in the overlapping region. That is, when the imager position determination section 212 determines that the amount of rotation of the imager 371 is equal to or greater than 90°, the imaging timing control section 213 outputs control information for the instruction of imaging only to the imager 372.

Hereinafter, "only one of the imager 371 and the imager 372 performs imaging at one imaging timing" is referred to as "one-sided imaging". In addition, "both of the imager 371 and the imager 372 perform imaging at one imaging timing" is referred to as "simultaneous imaging".

Figure 8:
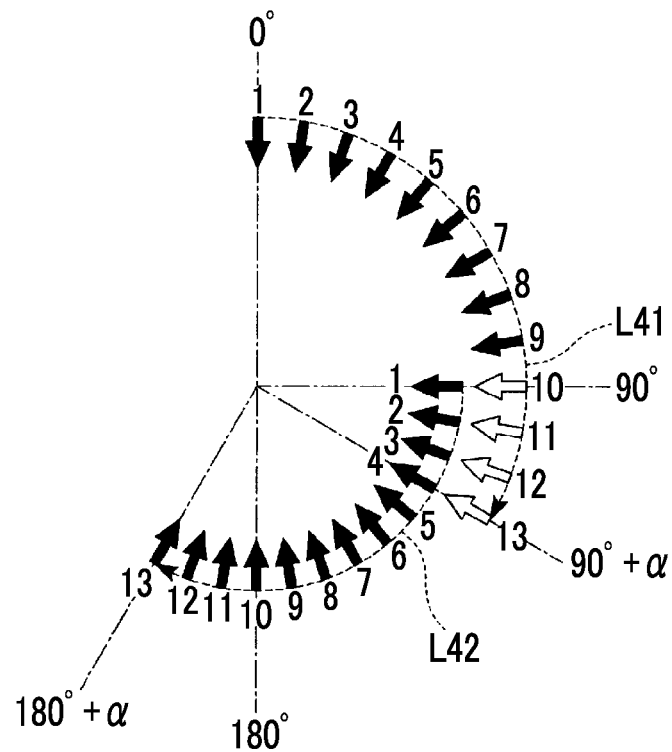
FIG. 8 is an explanatory diagram of a first example of the control of the imaging timing in the present embodiment.

FIG. 8 is an explanatory diagram of a first example of the control of the imaging timing. In the example shown in this diagram, 13 imaging timings are set while the imager 371 or the imager 372 rotates by 90°+fan angle α. Here, line L41 indicates the rotation range of the diagnostic X-ray source 341, and line L42 indicates the rotation range of the diagnostic X-ray source 342.

At the first to ninth imaging timings, the imaging timing control section 213 instructs the imager 371 and the imager 372 to perform simultaneous imaging.

On the other hand, the imager 371 is located in the overlapping region at the tenth and subsequent imaging timings. Therefore, even if the imager 371 stops imaging, the CT image reconstruction section 217 can acquire a radiographic image for the 180°+fan angle α. As a result, it is possible to acquire the information by emitting X-rays to all voxels from the respective directions in the range of 180° or more.

Therefore, at the tenth and subsequent imaging timings, the imaging timing control section 213 instructs only the imager 372 to perform imaging (one-sided imaging).

Thus, when the imager position determination section 212 determines that the amount of rotation of the imager 371 is equal to or greater than 90°, the imaging timing control section 213 instructs only the imager 372 to perform imaging (stops the imaging of the imager 371), thereby being able to reduce the radiation dose. In the example shown in FIG. 8, compared with a case where the imager 371 emits radiation even at the tenth to thirteenth imaging timings, it is possible to reduce the four-time radiation dose for the imager 371.

In addition, the imaging timing shown in FIG. 8 is an example for explanation, and is not limited thereto.

For example, the number of imaging timings whose arrival is detected by the imaging timing control section 213 is not limited to 13 times.

Alternatively, when the imager position determination section 212 determines that the amount of rotation of the imager 371 is equal to or greater than 90°, the imaging timing control section 213 may instruct the imager 371 and the imager 372 to perform simultaneous imaging at some imaging timings.

Figure 9:
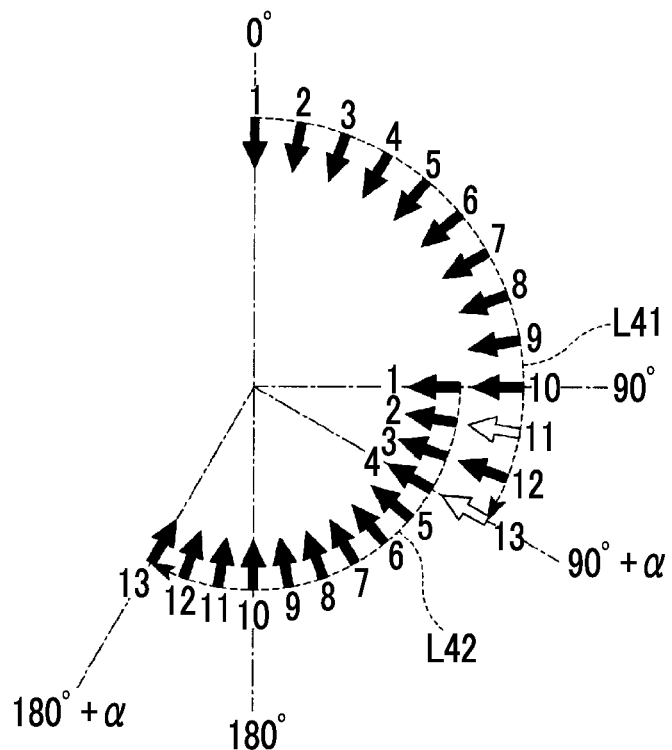
FIG. 9 is an explanatory diagram of a second example of the control of the imaging timing in the present embodiment.

FIG. 9 is an explanatory diagram of a second example of the control of the imaging timing. Similar to the case shown in FIG. 8, in the example shown in FIG. 9, 13 imaging timings are set while the imager 371 or the imager 372 rotates by 90°+fan angle α. In addition, similar to the case shown in FIG. 8, line L41 indicates the rotation range of the diagnostic X-ray source 341, and line L42 indicates the rotation range of the diagnostic X-ray source 342.

In addition, similar to the case shown in FIG. 8, the imaging timing shown in FIG. 9 is an example for explanation, and is not limited thereto.

In the example shown in FIG. 9, similar to the case shown in FIG. 8, at the first to ninth imaging timings, the imaging timing control section 213 instructs the imager 371 and the imager 372 to perform simultaneous imaging.

In addition, at the eleventh and thirteenth imaging timings of the tenth and subsequent imaging timings at which the imager 371 is located in the overlapping region, similar to the case shown in FIG. 8, the imaging timing control section 213 instructs only the imager 372 to perform imaging (one-sided imaging).

On the other hand, at the tenth and twelfth imaging timings, unlike the case shown in FIG. 8, the imaging timing control section 213 instructs the imager 371 and the imager 372 to perform simultaneous imaging.

As will be described later, the position specifying section 215 can specify the position of a position specification target (in the present embodiment, an affected part that is a target to which the therapeutic radiation B11 is to be emitted) in a three-dimensional manner due to the simultaneous imaging of the imager 371 and the imager 372. Therefore, as will be described later, the image correction section 216 can correct a radiographic image even if the position specification target moves in a direction of the diagnostic X-ray B21 or in a direction of the diagnostic X-ray B22.

Here, as a criterion for performing switching between one-sided imaging and simultaneous imaging by the imaging timing control section 213 in a state where the imager 371 is located in the overlapping region, various criteria can be used.

For example, when the imaging period is sufficiently shorter than the breathing cycle of the imaging target T11, the image correction section 216 can correct a radiographic image for the subject blur in the diagnostic X-ray direction due to the breathing of the imaging target T11 even if the position specifying section 215 does not specify a three-dimensional position every imaging timing.

For example, at an imaging timing up to a predetermined time after the position specifying section 215 specifies the three-dimensional position of the position specification target, the image correction section 216 may use the three-dimensional position. Alternatively, in a period of time for which the movement of the position specification target can be regarded as linear uniform motion after the position specifying section 215 specifies the three-dimensional position of the position specification target, the position specifying section 215 may calculate the three-dimensional position of the position specification target every imaging timing.

Therefore, when the imager 371 is located in the overlapping region, the imaging timing control section 213 may cause only the imager 372 to perform imaging (one-sided imaging) at a predetermined number (1 or more) of imaging timings after the position specifying section 215 succeeds in specifying the three-dimensional position of the position specification target.

Thus, when the imaging timing control section 213 detects the arrival of the imaging timing and causes both of the imager 371 and the imager 372 to perform imaging (simultaneous imaging) and the position specifying section 215 succeeds in specifying the three-dimensional position of the position specification target based on the obtained radiographic image, if the arrival of the next imaging timing is detected in a state where the imager position determination section 212 determines that the imager 371 is located in the overlapping region, the imaging timing control section 213 may cause only the imager 372 to perform imaging (one-sided imaging).

Alternatively, when the imaging period is short, once the position specification target is hidden by bone or the like in the radiographic image of the imager 371 or the imager 372, the state where the position specification target is hidden continues for a while. In the meantime, even if the imager 371 and the imager 372 perform simultaneous imaging, the position specifying section 215 may continuously fail to specify a three-dimensional position.

Therefore, when the imager 371 is located in the overlapping region, the imaging timing control section 213 may cause only the imager 372 to perform imaging (one-sided imaging) at a predetermined number (1 or more) of imaging timings after the position specifying section 215 fails to specify the three-dimensional position of the position specification target.

Thus, when the imaging timing control section 213 detects the arrival of the imaging timing and causes both of the imager 371 and the imager 372 to perform imaging (simultaneous imaging) and the position specifying section 215 fails to detect the image of the position specification target in at least one of the obtained radiographic images, if the arrival of the next imaging timing is detected in a state where the imager position determination section 212 determines that the imager 371 is located in the overlapping region, the imaging timing control section 213 may cause only the imager 372 to perform imaging (one-sided imaging).

Alternatively, the imaging timing control section 213 may store an imaging plan determined by a doctor or the like in advance, and perform switching between simultaneous imaging and one-sided imaging according to the imaging plan when the imager 371 is located in the overlapping region.

The imager image acquisition section 214 acquires a radiographic image (radiographic image data) captured by the imager 371 and a radiographic image (radiographic image data) captured by the imager 372 from the radiotherapy apparatus 3, and outputs the radiographic images to the position specifying section 215.

The position specifying section 215 specifies the three-dimensional position of the position specification target (hereinafter, will be described as an affected part) based on the radiographic image captured by the imager 371 and the radiographic image captured by the imager 372. That is, it is not possible to specify the position of the affected part in a depth direction from only one radiographic image, but the position specifying section 215 can also detect the position of the affected part in the depth direction by using another radiographic image that has been simultaneously captured from another direction.

For example, first, the position specifying section 215 specifies the position of an affected part by image matching (template matching) for each radiographic image obtained by simultaneous imaging of the imager 371 and the imager 372. Information (template) of the shape of the affected part for image matching is generated, for example, by a doctor based on the radiographic image (Roentgen image) captured in advance, and is given to the position specifying section 215.

When the position specifying section 215 succeeds in specifying the position of the affected part in both of the radiographic image captured by the imager 371 and the radiographic image captured by the imager 372, the position specifying section 215 specifies the three-dimensional position of the affected part based on the position information of the affected part in both of the images. As a method used when the position specifying section 215 specifies the three-dimensional position of the affected part, it is possible to use known methods, such as a method disclosed in Japanese Patent No. 404952.

The image correction section 216 corrects the position of the affected part in the radiographic image captured by the imager 371 or the radiographic image captured by the imager 372.

Here, in the radiographic image captured by the imager 371 or the imager 372, from the difference in imaging timing, the position of the affected part may shift due to the breathing of the imaging target T11 or the like. Due to the shift of the affected part, there is a possibility that the accuracy of the CT image will be lowered. Therefore, the image correction section 216 corrects the position of the affected part (performs correction for acquiring a radiographic image close to a radiographic image when the affected part does not move), thereby reducing the lowering of accuracy of the CT image.

Specifically, the image correction section 216 moves the position of an image of the affected part in the radiographic image.

Figure 10:
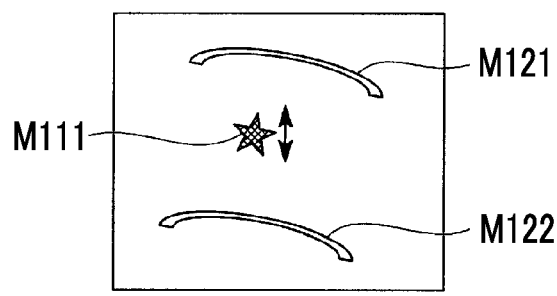
FIG. 10 is a diagram showing an example of a radiographic image when the position of an affected part is shifted in the present embodiment.

FIG. 10 is a diagram showing an example of a radiographic image when the position of an affected part is shifted. An image M111 of an affected part and bone images M121 and M122 are included in the radiographic image shown in this diagram. In the example shown in FIG. 10, the position of the affected part moves according to the breathing of the imaging target T11. On the other hand, the position of the bone shown in the image M121 or M122 does not move.

Therefore, the image correction section 216 moves the position of the affected part image while keeping the positions of the bone images M121 and M122 in the radiographic image, thereby reducing the influence of the shift of the affected part position on the CT image. As a method used when the image correction section 216 moves the position of the affected part image, it is possible to use known methods, such as a method using an optical flow shown in Japanese Unexamined Patent Application Publication 2001-259059. In the method using the optical flow, the image correction section 216 translates the position of the affected part image to a shift vector and an inverse vector of the affected part shown in the optical flow.

When the information of the three-dimensional position of the affected part is acquired from the position specifying section 215, the image correction section 216 also corrects the radiographic image for the movement of the position of the affected part in the diagnostic X-ray direction.

Figure 11A:
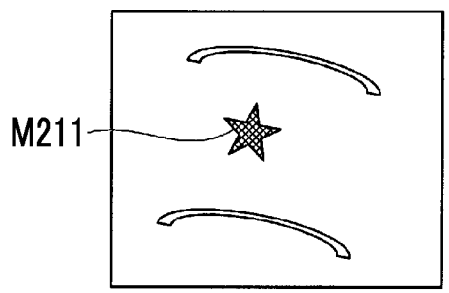
FIG. 11A is an explanatory diagram showing an example of the correction of a radiographic image for the movement of the position of the affected part in a diagnostic X-ray direction that is performed by an image correction section in the present embodiment.
Figure 11B:
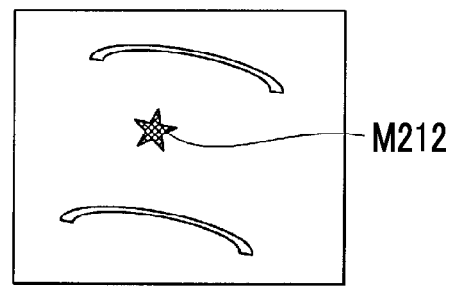
FIG. 11B is an explanatory diagram showing an example of the correction of a radiographic image for the movement of the position of the affected part in a diagnostic X-ray direction that is performed by the image correction section in the present embodiment.

FIGS. 11A and 11B are explanatory diagrams showing an example of the correction of a radiographic image for the movement of the position of the affected part in the diagnostic X-ray direction that is performed by the image correction section 216. FIG. 11A shows an example of a radiographic image before correction, and FIG. 11B shows an example of a radiographic image after correction.

In the example shown in FIGS. 11A and 11B, the affected part is shifted to the side of the diagnostic X-ray source 340. For this reason, in the image shown in FIG. 11A, an image M211 of the affected part is relatively large. Therefore, the image correction section 216 performs correction for reducing the image of the affected part as an image M212 of the affected part in FIG. 11B, according to a case where the affected part is located closer to the sensor array 360 side. As a method of correcting the radiographic image for the movement of the position of the affected part in the diagnostic X-ray direction that is performed by the image correction section 216, it is possible to use known methods, such as a method of calculating the optical flow in a three-dimensional manner.

In addition, since the image correction section 216 calculates the optical flow in a three-dimensional manner, it is possible to eliminate the influence of the shift of the imaging angle at each imaging timing.

For example, in FIG. 9, a shift in the imaging direction occurs between a radiographic image captured by the imager 371 at the first imaging timing and a radiographic image captured by the imager 371 at the second imaging timing. The shift in the imaging direction may become an error when calculating the two-dimensional optical flow. In contrast, when the position specifying section 215 specifies the position of the affected part with the three-dimensional coordinates fixed to the imaging target T11, the three-dimensional coordinates are fixed irrespective of the imaging direction. Accordingly, it is possible to eliminate the influence of the shift in the imaging direction when calculating the optical flow.

In addition, based on the radiographic images obtained by simultaneous imaging, the image correction section 216 may correct the direction of the rotation axis A12 (body axis direction).

For example, due to the contour of the image of the affected part being unclear, or due to deformation of the affected part, or due to the shadow of other organs being reflected on the affected part, there is a possibility that an error may occur in the direction of the rotation axis A12 when calculating the position of the affected part by image matching for determining the position of the affected part.

In such a case, for example, by taking the average of the position of the affected part in the direction of the rotation axis A12 in the radiographic image captured by the imager 371 and the radiographic image captured by the imager 372 in simultaneous imaging, it is possible to reduce the magnitude of the error.

In addition, when an organ hidden by the affected part is visible by the correction of the radiographic image for the movement of the position of the affected part in the diagnostic X-ray direction, the image correction section 216 may acquire an image of the organ from another radiographic image and add the image to the radiographic image to be corrected.

The treatment control unit 220 controls the radiotherapy apparatus 3 when emitting the therapeutic radiation B11. For example, the treatment control unit 220 performs various kinds of control, such as the control of the position of the therapeutic radiation emission unit 331, the control of the emission time of the therapeutic radiation B11, or the control of the multi-leaf collimator 332, according to the treatment plan made by the doctor based on the CT image generated by the CT image reconstruction section 217.

As the radiotherapy apparatus controller 2, for example, a computer can be used. In this case, functions of each unit of the radiotherapy apparatus controller 2 can be realized by causing a central processing unit (CPU) provided in the computer to read a program from a storage device provided in the computer and execute the program.

However, it is also possible to use apparatuses other than the computer as the radiotherapy apparatus controller 2. For example, each unit of the radiotherapy apparatus controller 2 can be formed by dedicated hardware.

Next, the operation of the radiotherapy system 1 when generating a CT image will be described with reference to FIG. 12.

FIG. 12 is a flowchart showing the procedure of the process performed by the imaging processing unit 210. The imaging processing unit 210 starts the process shown in this diagram when the radiotherapy apparatus controller 2 receives a user operation for instructing the generation of a CT image.

In the process shown in FIG. 12, the imaging processing unit 210 performs a calibration first (step S101). For example, the imager rotation control section 211 adjusts the position of each of the imager 371 and the imager 372 to the initial position, and adjusts the direction of the irradiation axis of each of the imager 371 and the imager 372 to a direction passing through the isocenter P11. In addition, the imaging timing control section 213 performs a response performance calibration for matching the response performance of the sensor array 361 and the sensor array 362.

Then, the imager rotation control section 211 controls the traveling driving device to rotate the traveling gantry 313 at a fixed speed (step S102).

Then, the imaging timing control section 213 determines whether or not the imaging timing has arrived (step S103). Specifically, the imaging timing control section 213 has a timer function, and detects the arrival of the imaging timing every predetermined time set in advance as an imaging period.

When the imaging timing control section 213 determines that the imaging timing has arrived in step S103 (step S103: YES), the imaging timing control section 213 selects one-sided imaging or simultaneous imaging (step S111). Specifically, as described above, when the imager position determination section 212 determines that the imager 371 is not located in the overlapping region, the imaging timing control section 213 instructs the imager 371 and the imager 372 to perform simultaneous imaging. On the other hand, when the imager position determination section 212 determines that the imager 371 is located in the overlapping region, the imaging timing control section 213 selects one-sided imaging or simultaneous imaging based on the imaging plan acquired in advance or a program set in advance, and gives an imaging instruction according to the selection.

When one or both of the imager 371 and the imager 372 capture radiographic images according to the instruction of the imaging timing control section 213, the imager image acquisition section 214 acquires the radiographic images (radiographic image data) (step S112).

When the imager 371 and the imager 372 perform simultaneous imaging, the position specifying section 215 calculates the three-dimensional position of the affected part as described above (step S113).

Then, the image correction section 216 corrects the position of the affected part as described above for the image captured by the imager 371 or the image captured by the imager 372. In particular, when the information of the three-dimensional position of the affected part is acquired from the position specifying section 215, the image correction section 216 also corrects the position of the affected part for the movement of the affected part in the diagnostic X-ray direction (step S114).

Then, the CT image reconstruction section 217 performs a calculation for reconstructing the CT image (step S115). Specifically, the CT image reconstruction section 217 performs the above-described back projection based on the projection image corrected by the image correction section 216.

Then, the imaging processing unit 210 determines whether or not the imaging at all angles has been completed (step S116). For example, the imager position determination section 212 acquires the amount of rotation of the traveling gantry 313, and determines whether or not the amount of rotation is equal to or greater than $90°+\alpha$.

When it is determined that the imaging at all angles has not been completed (step S116: NO), the process returns to step S102.

On the other hand, when it is determined that the imaging at all angles has been completed (step S116: YES), the CT image reconstruction section 217 reconstructs a tomographic image by calculating the amount of transmitted radiation for each voxel from the result of the back projection, and outputs the obtained tomographic image (step S121). For example, the CT image reconstruction section 217 stores the tomographic image in a storage device provided in the radiotherapy apparatus controller 2, and displays the tomographic image on a display screen provided in the radiotherapy apparatus controller 2.

In this case, the imager rotation control section 211 ends the output of the rotation instruction in step S102, and accordingly, the traveling gantry 313 is stopped (rotation is ended).

Then, the process shown in FIG. 12 is ended.

On the other hand, when the imaging timing control section 213 determines that the imaging timing has not arrived in step S103 (step S103: NO), the process proceeds to step S116.

As described above, the imaging timing control section 213 causes only the imager 372 to perform imaging in at least one imaging timing whose arrival is detected in a state where the imager position determination section 212 determines that the imager 371 is located in the overlapping region.

Since the imaging timing control section 213 causes only the imager 372 to perform imaging, it is possible to reduce the radiation dose equivalent to the radiation from the imager 371 at the imaging timing.

In particular, in a state where the imager 371 is not located in the overlapping region, the imaging timing control section 213 causes the imager 371 and the imager 372 to perform simultaneous imaging, so that a radiographic image of $180°+$fan angle $\alpha$ can be captured. In this regard, the imaging timing control section 213 can reduce the radiation dose without lowering the accuracy of the CT image.

For example, when the imaging timing control section 213 detects the arrival of the imaging timing and causes the imager 371 and the imager 372 to perform simultaneous imaging and the position specifying section 215 succeeds in specifying the three-dimensional position of the position specification target based on the obtained radiographic image, if the arrival of the next imaging timing is detected in a state where the imager position determination section 212 determines that the imager 371 is located in the overlapping region, the imaging timing control section 213 may cause only the imager 372 to perform imaging (one-sided imaging).

In this case, at the imaging timing at which the imager 372 has performed one-sided imaging, the image correction section 216 can perform correction for the movement of the position specification target in the diagnostic X-ray direction based on the three-dimensional position of the position specification target specified by the position specifying section 215 based on simultaneous imaging or based on a new three-dimensional position calculated from the three-dimensional position.

In this regard, it is possible to reduce the radiation dose while increasing the accuracy of the CT image.

Alternatively, when the imaging timing control section 213 detects the arrival of the imaging timing and causes the imager 371 and the imager 372 to perform simultaneous imaging and the position specifying section 215 fails to detect the image of the position specification target in at least one of the obtained radiographic images, if the arrival of the next imaging timing is detected in a state where the imager position determination section 212 determines that the imager 371 is located in the overlapping region, the imaging timing control section 213 may cause only the imager 372 to perform imaging (one-sided imaging).

In this case, since the imaging timing control section 213 stops simultaneous imaging at an imaging timing at which there is a high possibility that the position specifying section 215 will fail to specify the three-dimensional position of the position specification target even if the imager 371 and the imager 372 perform simultaneous imaging, it is possible to reduce the radiation dose.

Alternatively, the imaging timing control section 213 causes only the imager 372 to perform imaging (one-sided imaging) at all of the imaging timings whose arrival is detected in a state where the imager position determination section 212 determines that the imager 371 is located in the overlapping region.

In this manner, it is possible to further reduce the radiation dose.

In addition, a control target in the present embodiment is not limited to the radiotherapy apparatus. For example, a CT dedicated apparatus can also be the control target in the present embodiment. As the configuration of a CT dedicated apparatus, for example, it is possible to adopt a configuration in which each unit (the therapeutic radiation emission unit 331, the multi-leaf collimator 332, or the sensor array 351) for emission of the therapeutic radiation B11 has been removed from the configuration shown in FIG. 2. In addition, for the configuration on the controller side, it is possible to adopt a configuration in which the treatment control unit 220 has been removed from the configuration shown in FIG. 4.

In addition, the imager 371 may correspond to an example of the second imager, and the imager 372 may correspond to an example of the first imager. In this case, only the imager 371 may perform one-sided imaging in at least a part of the timing at which the imager 372 is located in the overlapping region, so that the imaging from the overlapping region is performed by the imager 371.

In addition, both of the imager 371 and the imager 372 may correspond to any example of the first imager and the second imager. For example, imaging in the overlapping region may be alternately performed by the imager 371 and the imager 372.

In addition, as long as the rotation range of the imager 371 and the rotation range of the imager 372 overlap each other, the angle between the irradiation axis of the imager 371 and the irradiation axis of the imager 372 with the rotation axis A12 as a reference is not limited to 90° described above, and may be an arbitrary angle.

In addition, the number of imagers provided in the radiotherapy apparatus or the CT dedicated apparatus that is a control target is not limited to 2 described above, and three or more imagers may be provided. For example, the radiotherapy apparatus 3 may include a third imager in addition to the imagers 371 and 372. In this case, for example, the angle between the irradiation axis of the imager 371 and the irradiation axis of the imager 372 with the rotation axis A12 as a reference may be 60°, and the angle between the irradiation axis of the imager 372 and the irradiation axis of the third imager with the rotation axis A12 as a reference may be 60°.

By arranging the imagers as described above, if the traveling gantry 313 rotates 60° or more, a rotation range when the rotation ranges of the three imagers are combined is equal to or greater than 180°. Therefore, it is possible to reduce the time required to capture a radiographic image. In addition, in the same manner as described with reference to FIG. 7, an overlapping region of the rotation ranges of the imagers occurs from the relationship with the fan angle. In the overlapping region, the imaging timing control section 213 can select one of imaging by one imager, imaging by two imagers, and imaging by three imagers every imaging timing.

In addition, it is preferable that both the irradiation axis of the imager 371 and the irradiation axis of the imager 372 pass through the vicinity of the isocenter P11, however, the irradiation axis of the imager 371 and the irradiation axis of the imager 372 do not necessarily need to pass through the isocenter P11. In addition, the irradiation axis of the imager 371 and the irradiation axis of the imager 372 do not necessarily need to cross each other (may be in a relationship of twisted position).

In addition, as described above, a computer can be used as the radiotherapy apparatus controller 2. Accordingly, the processing of each unit may be performed by recording a program for realizing the functions of all or some of the units of the radiotherapy apparatus controller 2 in a computer-readable recording medium, reading the program recorded in the recording medium into a computer system, and executing the read program. In addition, the "computer system" referred to herein may include an OS or hardware, such as a peripheral device.

In addition, the "computer system" may also include a homepage presenting environment (or display environment) if a WWW system is used.

In addition, examples of the "computer-readable recording medium" include portable media, such as a flexible disk, a magneto-optic disc, a ROM, and a CD-ROM, and a storage device, such as a hard disk built in a computer system. In addition, examples of the "computer-readable recording medium" may include a recording medium that stores a program dynamically for a short period of time like a network, such as the Internet, or a communication line when a program is transmitted through a communication line, such as a telephone line, and include a recording medium that stores a program for a predetermined period of time like a volatile memory in a computer system that serves as a server or a client in this case. In addition, the above program may be a program for realizing some of the functions described above or may be a program capable of realizing the above functions by combination with a program already recorded in the computer system.

While the embodiment of the present invention has been described in detail with reference to the diagrams, the specific configuration is not limited to the above-described embodiment, and various changes may be made in design without departing from the spirit of the present invention.

INDUSTRIAL APPLICABILITY

The present invention relates to an imaging controller of an imaging apparatus which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle. The imaging controller includes: an imager position determination section that determines whether or not the first imager is located in an overlapping region where a rotation range of the first imager and a rotation range of the second imager overlap each other when the rotation mechanism rotates the first and second imagers by an angle greater than the predetermined angle; and an imaging timing control section that causes one or both of the first and second imagers to perform imaging when arrival of an imaging timing is detected and that causes only the second imager to perform imaging in at least one imaging timing whose arrival has been detected in a state where the imager position determination section determines that the first imager is located in the overlapping region.

According to the present invention, it is possible to reduce the radiation dose.

REFERENCE SIGNS LIST

1: radiotherapy system
2: radiotherapy apparatus controller
3: radiotherapy apparatus
210: imaging processing unit
211: imager rotation control section
212: imager position determination section
213: imaging timing control section
214: imager image acquisition section
215: position specifying section
216: image correction section
217: CT image reconstruction section
220: treatment control unit
311: rotary driving unit
312: O ring
313: traveling gantry
321: swing mechanism
330: irradiation unit
331: therapeutic radiation emission unit
332: multi-leaf collimator
340, 341, 342: diagnostic X-ray source
351, 360, 361, 362: sensor array
381: couch
382: couch driving unit

The invention claimed is:

1. An imaging controller of an imaging apparatus which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle, the imaging controller comprising:
   an imager position determination section that determines whether or not the first imager is located in an overlapping region where a rotation range of the first imager and a rotation range of the second imager overlap each other when the rotation mechanism rotates the first and second imagers by an angle greater than the predetermined angle;
   an imaging timing control section that causes at least one of the first and second imagers to perform imaging when arrival of an imaging timing is detected and that causes only the second imager to perform imaging in at least one imaging timing whose arrival is detected in a state where the imager position determination section determines that the first imager is located in the overlapping region; and
   a position specifying section that specifies a three-dimensional position of a position specification target based on a radiographic image captured by the first imager and a radiographic image captured by the second imager,
   wherein, when the imaging timing control section detects arrival of an imaging timing and causes the first and second imagers to perform imaging and the position specifying section fails to detect an image of the position specification target in at least one of obtained radiographic images to thereby fail to specify the three-dimensional position of the position specification target, the imaging timing control section causes only the second imager to perform imaging at a predetermined number of an imaging timing after the position specifying section fails to specify the three-dimensional position of the position specification target in a state where the imager position determination section determines that the first imager is located in the overlapping region.

2. The imaging controller according to claim 1,
   wherein, when the imaging timing control section detects arrival of an imaging timing and causes the first and second imagers to perform imaging and the position specifying section succeeds in specifying the three-dimensional position of the position specification target based on the obtained radiographic images, if arrival of a next imaging timing is detected in a state where the imager position determination section determines that the first imager is located in the overlapping region, the imaging timing control section causes only the second imager to perform imaging.

3. An imaging system, comprising:
   an imaging apparatus which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle;
   an imaging controller configured to include an imager position determination section that determines whether or not the first imager is located in an overlapping region where a rotation range of the first imager and a rotation range of the second imager overlap each other when the rotation mechanism rotates the first and second imagers by an angle greater than the predetermined angle and an imaging timing control section that causes at least one of the first and second imagers to perform imaging when arrival of an imaging timing is detected and that causes only the second imager to perform imaging in at least one imaging timing whose arrival is detected in a state where the imager position determination section determines that the first imager is located in the overlapping region; and a position specifying section that specifies a three-dimensional position of a position specification target based on a radiographic image captured by the first imager and a radiographic image captured by the second imager, wherein, when the imaging timing control section detects arrival of an imaging timing and causes the first and second imagers to perform imaging and the position specifying section fails to detect an image of the position specification target in at least one of obtained radiographic images to thereby fail to specify the three-dimensional position of the position specification target, the imaging timing control section causes only the second imager to perform imaging at a predetermined number of an imagine timing after the position specifying section fails to specify the three-dimensional position of the position specification target in a state where the imager position determination section determines that the first imager is located in the overlapping region.

4. An imaging control method of an imaging controller of an imaging apparatus which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle, the method comprising:

an imager position determination step of determining whether or not the first imager is located in an overlapping region where a rotation range of the first imager and a rotation range of the second imager overlap each other when the rotation mechanism rotates the first and second imagers by an angle greater than the predetermined angle;

an imaging timing control step of causing at least one of the first and second imagers to perform imaging when arrival of an imaging timing is detected and causing only the second imager to perform imaging in at least one imaging timing whose arrival is detected in a state where it is determined that the first imager is located in the overlapping region in the imager position determination step; and a position specifying step of specifying a three-dimensional position of a position specification target based on a radiographic image captured by the first imager and a radiographic image captured by the second imager, wherein, when arrival of an imaging timing is detected and the first and second imagers are caused to perform imaging in the imaging timing control step and detecting an image of the position specification target in at least one of obtained radiographic images is failed to thereby fail to specify the three-dimensional position of the position specification target in the position specifying step, only the second imager is caused to perform imaging at a predetermined number of an imaging timing in the imaging timing control step after being failed to specify the three-dimensional position of the position specification target in the position specifying step in a state where the first imager is determined to be located in the overlapping region in the imager position determination step.

5. A program causing a computer as an imaging controller of an imaging apparatus, which includes first and second imagers for capturing a radiographic image by emitting a cone beam toward a rotation axis and a rotation mechanism for rotating the first and second imagers integrally around the rotation axis and in which an angle between an irradiation axis of the first imager and an irradiation axis of the second imager with the rotation axis as a reference is a predetermined angle, to execute:

an imager position determination step of determining whether or not the first imager is located in an overlapping region where a rotation range of the first imager and a rotation range of the second imager overlap each other when the rotation mechanism rotates the first and second imagers by an angle greater than the predetermined angle;

an imaging timing control step of causing at least one of the first and second imagers to perform imaging when arrival of an imaging timing is detected and causing only the second imager to perform imaging in at least one imaging timing whose arrival is detected in a state where it is determined that the first imager is located in the overlapping region in the imager position determination step; and a position specifying step of specifying a three-dimensional position of a position specification target based on a radiographic image captured by the first imager and a radiographic image captured by the second imager, wherein, when arrival of an imaging timing is detected and the first and second imagers are caused to perform imaging in the imaging timing control step and detecting an image of the position specification target in at least one of obtained radiographic images is failed to thereby fail to specify the three-dimensional position of the position specification target in the position specifying step, only the second imager is caused to perform imaging at a predetermined number of an imaging timing in the imaging timing control step after being failed to specify the three-dimensional position of the position specification target in the position specifying step in a state where the first imager is determined to be located in the overlapping region in the imager position determination step.

* * * * *